US006767565B2

(12) United States Patent
Shukla et al.

(10) Patent No.: US 6,767,565 B2
(45) Date of Patent: Jul. 27, 2004

(54) PROCESS FOR OBTAINING LIGNAN

(75) Inventors: Rishi Shukla, Decatur, IL (US);
Ahmad K. Hilaly, Springfield, IL (US);
Kevin M. Moore, Mount Zion, IL (US)

(73) Assignee: Archer Daniels Midland Company, Decatur, IL (US)

( * ) Notice: Subject to any disclaimer, the term of this patent is extended or adjusted under 35 U.S.C. 154(b) by 14 days.

(21) Appl. No.: 10/101,423

(22) Filed: Mar. 20, 2002

(65) Prior Publication Data

US 2003/0055227 A1 Mar. 20, 2003

Related U.S. Application Data

(60) Provisional application No. 60/277,632, filed on Mar. 22, 2001.

(51) Int. Cl.$^7$ .............................................. A61K 35/78

(52) U.S. Cl. ...................................... 424/768; 424/725

(58) Field of Search ................................. 424/768, 725

(56) References Cited

U.S. PATENT DOCUMENTS

| 5,705,618 | A | 1/1998 | Westcott et al. ............ 530/500 |
| 5,837,256 | A | 11/1998 | Clark et al. ............... 424/195.1 |
| 6,261,565 | B1 * | 7/2001 | Empie et al. |

FOREIGN PATENT DOCUMENTS

| EP | 0 389 631 A1 | 10/1990 |
| WO | WO 96/30468 A2 | 10/1996 |
| WO | WO 97/14670 A1 | 4/1997 |
| WO | WO 00/19842 A1 | 4/2000 |
| WO | WO 00/78771 A1 | 12/2000 |

OTHER PUBLICATIONS

MacRae, W.D., and Towers, G.H.N., "Biological activities of lignans," *Phytochemistry* 23:1207–1220, Pergamon Press, Ltd. (1984).
Bakke, J.E. and Klosterman, H.J., "A New Diglucoside from Flaxseed," *Proceedings of the North Dakota Academy of Science* 10:18–22, University of North Dakota and the North Dakota Agricultural College (1956).
Demark–Wahnefried, W., et al., "Pilot Study of Dietary Fat Restriction and Flaxseed Supplementation in Men with Prostate Cancer before Surgery: Exploring the Effects on Hormonal Levels, Prostate–Specific Antigen, and Histopathologic Features," *Adult Urol.* 58:47–52, Elsevier Science Inc. (Jul. 2001).
Kitts, D.D., et al., "Antioxidant activity of the flaxseed lignan secoisolariciresinol diglycoside and its mammalian lignan metabolites enterodiol and enterolactone," *Mol. Cell. Biochem.* 202:91–100, Kluwer Academic Publishers (1999).
Mazza, G. and Oomah, B.D., "Flaxseed, Dietary Fiber, and Cyanogens," in *Flaxseed In Human Nutrition*, Cunnane, S.C. and Thompson, L.U., eds., AOCS Press, Champaign, IL, pp. 56–81 (1995).

Morton, M.S., et al., "Lignans and Isoflavonoids in Plasma and Prostatic Fluid in Men: Samples From Portugal, Hong Kong, and the United Kingdom," *The Prostate* 32:122–128, Wiley–Liss, Inc. (1997).
Muir, A.D., et al., "Flax Lignans—Recent Developments in the Analysis of Lignans in Plant and Animal Tissues," in *Proceedings of the 58$^{th}$ Flax Institute of the United States*, pp. 23–32, Fargo, North Dakota, Mar. 23–25 (2000).
Prasad, K., "Dietary flax seed in prevention of hypercholesterolemic atherosclerosis," *Atherosclerosis* 132:69–76, Elsevier Science Ireland Ltd. (1997).
Prasad, K.–M.R., et al., "Novel Method of Gene Delivery to Pancreatic Beta Cells," *Diabetes* 48:A58, Abstract No. 0248, The American Diabetes Association (1999).
Rickard, S.E., et al., "Anticancer Effects and Availability of Flaxseed Lignans," in *Proceedings of the 57$^{th}$ Flax Institute of the United States*, pp. 8–14, Fargo, North Dakota, Mar. 26–28 (1998).
Setchell, K.D.R., et al., "The definitive identification of the lignans trans–2,3–bis (3–hydroxybenzyl)–γ–butyrolactone and 2,3–bis (3–hydroxybenzyl)butane–1,4–diol in human and animal urine," *Biochem. J.* 197:447–458, The Biochemical Society (1981).
Shukla, R., "Production of Zein from Dry Milled Corn by Solvent Extraction and Ultrafiltration," Thesis for Doctor of Philosophy in Agricultural Engineering in the Graduate College of the University of Illinois at Urbana–Champaign (2000).
Smith, J., C.R., et al., "Linustatin and Neolinustatin: Cyanogenic Glycosides of Linseed Meal That Protect Animals against Selenium Toxicity," *J. Org. Chem.* 45:507–510, The American Chemical Society (1980).
Sung, M.–K., et al., "Mammalian Lignans Inhibit the Growth of Estrogen–Independent Human Colon Tumor Cells," *Anticancer Res.* 18:1405–1408, International Journal of Cancer Research and Treatment (1998).
Thompson, L.U., et al., "Antitumorigenic Effect of a Mammalian Lignan Precursor From Flaxseed," *Nutr. Cancer* 26:159–165, Lawrence Erlbaum Associates, Inc. (1996).
Thompson, L.U., "Flaxseed, Lignans, and Cancer," in *Flaxseed in Human Nutrition*, Cunnane, S.C. and Thompson, L.U., eds., AOCS Press, Champaign, IL, pp. 219–236 (1995).
Westcott, N.D., and Muir, A.D., "Medicinal Lignans from Flaxseed: Isolation and Purification," in *Phytochemicals and Phytopharmaceuticals*, Shahidi, F. and C.–T., Ho, eds., AOCS Press, Champaign, IL, pp. 122–131 (Dec. 2000).

* cited by examiner

Primary Examiner—Christopher R. Tate
(74) Attorney, Agent, or Firm—Kirkpatrick & Lockhart LLP

(57) ABSTRACT

Process for obtaining lignan from plant material by extraction with an extraction solvent and separation of the liquid fraction from the plant material. The separated liquid fraction containing the lignan product is subjected to further processing to remove cyanogenic sugars and other impurities. The resulting lignan containing product may be formulated for the treatment of various conditions, such as cancer, diabetes, hypertension, lupus, and atherosclerosis.

17 Claims, 3 Drawing Sheets

PROCESS FOR OBTAINING LIGNAN

CROSS REFERENCE TO RELATED APPLICATIONS

This application claims the benefit of U.S. Provisional Application No. 60/277,632, filed Mar. 22, 2001, the disclosure of which is incorporated herein by reference in its entirety.

BACKGROUND OF THE INVENTION

1. Field of the Invention

The present invention is directed to methods of obtaining lignan from plant materials, particularly flax and flaxseed. The invention is also directed to compositions containing lignan obtained from the methods described herein.

2. Background Art

Lignans are secondary plant metabolites, which are produced from shikimic acid via the phenylpropanoid pathway. They develop from flavonoid precursors and are responsible for conferring resistance to plants against pathogens and predators. Lignans are defined to be compounds possessing a 2,3-dibenzylbutane structure and include matairesinol, secoisolaricinesinol, lariuresinol, isolariciresinol, nordihydroguaiaretic acid, pinoresinol, olivil and other compounds, and modifications thereof, including diglucosides such as but not limited to herbacetin 3,8-0-diglucopyanoside, herbacetin 3,7-0-dimethyl ether and Kaempferol 3,7-0-diglucopyranoside. Diglycerides are known precursors of two important mammalian lignans dibenzylbutyrolactone enterolactone and dibenzyl butane enterodiol (Setchell, et al., Biochem J. 197:447–458 (1981)).

Flaxseed (Linum usitatissimum) is potentially the richest source of phytoestrogens including lignans. The primary lignan found in flaxseed is 2,3-bis (3-methoxy-4-hydroxybenzyl) butane-1,4-diol (secoisolariciresinol) which is stored as the conjugate secoisolariciresinol diglucoside (SDG) in its native state in the plant. Flax seed contains levels of these phytoestrogens which are 75–800 times greater than any other plant food. The plant lignan, catecholic nordihydroguaiaretic acid, is a potent antioxidant previously used by the food industry.

Plant phenolic compounds occur as free monomers or in combination with other phytochemicals, thereby forming esters or glycosides. Phenolic acids are known to have antioxidant activity. The major phenolic constituents of flaxseed are reported to be cournaric acid (4-glucosyl-cinnamic acid) caffeic acid (3-hydroxy-4-glucosyl-cinnamic acid), ferulic acid (3-methoxy-4glucosyl cinnamic acid) and hydroxy methyl glutamic acid. These compounds have antioxidant and hyperchlolesterernic properties.

Numerous reports in literature have documented the phytochemical benefits of flaxseed lignans. Rickard et al. reported that feeding purified lignan at 5% flaxseed diet levels significantly reduces colon and mammary carcinogenesis in animals (Proceedings of the 57th Flax Institute of the United States, (Fargo, N. Dak.): 8–13 (1998)). Demark-Wahnefried et al. also reported that flaxseed supplementation may have a beneficial effect on prostate cancer biology (Demark-Wahnefried et al., Adult Urology 58(1): 47–52 (2001)).

Additionally, it has been reported that lignans prevent the development of Type I and Type II diabetes by 71% (Prasad, K. Proc. of the American Diabetes Association, (1999)), act as a hypotensive agent with ability to lower blood pressure without affecting heart rate (U.S. patent application Ser. No. 60/140,972, filed Jun. 16, 1999), provide benefits against Lupus Nephritis (U.S. Ser. No. 5,827,256), and reduce development of hypercholesterolemic atherosclerosis in animals (Atherosclerosis 132:69–76(1997)), along with numerous reports on the potential antioxidant (Mol. & Cell. Biochem., 202:91–100 (1999)) and anticancer properties (Anticancer Research 18:1405–1408 (1998)).

Flaxseed, in whole, ground or defatted form has been incorporated into animal feeds and food products such as breads, cookies, bagels and muffins. It has also been used for supplementing fiber levels in meat products (WO 00/19842). However, the amounts which can be used are regulated since high oil content of flax and the presence of mucilage contribute to excessive caloric intake and laxation (WO 96/30468).

One of the major problems associated with using flax in foods is the toxicity associated with cyanogenic glycosides present in flaxseed. Cyanogenic glycosides are nitrogenous secondary plant metabolites which if consumed in excess over a long period of time can result in goitrogenic problems and damage to human organs. These glycosides are important natural toxicants in both animal and human nutrition. They have been associated with flaxseed's unique property of protecting animals against the toxic effects of ingested selenium (Smith, et al., J Org. Chem. 45:507–510 (1980)). The major cyanogenic glycosides present in flaxseed are linustatin, neolinustatin and linamarin with linustatin accounting for 54–76% of the total cyanogenic glycoside content. Defatting of flax meal with hexane is known to produce an enrichment of all individual cyanogenic glycosides on equal weight basis in the meal (Maaza & Oomah, in Flaxseed in Human Nutrition, Cunnane & Thomson eds. AOCS Press, Champaign, Ill. 1995). Therefore, it is important to separate the cyanogenic glycosides from other compounds present in flax.

Methods for the preparation of lignans and other phenolic compound have been reported in literature. In 1956 Bakke and Klosterman described a process for extracting lignan from defatted flax using methanol dioxane (Proceedings of the North Dakota Academy of Sciences 10:18–22 (1956)). However, lignans are known to occur as a "complex" in flax with cinnamic acid glucosides and other compounds. Hence, lignans have originally been referred to as a "polymer" in flax. Sodium and barium methoxides have been used for methanolysis to release lignans free of other compounds (Blake & Klosterman; Thompson et al., Nutr. Cancer 26:59–165 (1996)). Almost all of the lignans present in flaxseed occur as components of a soluble ester-linked complex and do not occur as free glycosides or aglycone. (Muir et al. Proc. of the 58th Flax Institute of the US, Fargo, N. Dak., 1999). A detailed review of the various methods of extracting lignan and cinnamic acids can be found in Muir, supra. U.S. Pat. No. 5,705,618 and PCT Applications WO 96/30468 and WO 00/78771 also described methods of preparing lignan containing complexes. However, these processes suffer from drawbacks in that they cannot be scaled up for commercialization due to difficulty in achieving the desired separation and purity without involving complex solvent systems, such as ethyl acetate/water, and are difficult to separate using chromatographic techniques or employ expensive methods such as size exclusion chromatography.

BRIEF SUMMARY OF THE INVENTION

It is a general objective of this invention to provide a process for obtaining lignans from plant materials. The invention provides a process for obtaining lignan comprising:

(a) contacting a lignan containing plant material with an extraction solvent to obtain an extraction solution comprising a lignan containing extract and the extraction solvent;

(b) separating plant material solids from said extraction solution;

(c) reducing microbial component content in said extraction solution obtained in (b);

(d) removing from 0 to 100% of the extraction solvent from the extraction solution, while simultaneously adding an aqueous diluent to the extraction solution;

wherein a lignan is obtained therefrom.

The invention further provides a process for obtaining lignan comprising:

(a) contacting a lignan containing plant material with an extraction solvent to obtain an extraction solution comprising a lignan containing extract and the extraction solvent;

(b) separating plant source solids from said extraction solution;

(c) reducing microbial component content in said extraction solution obtained in (b);

(d) contacting the extraction solution obtained in (c) with an adsorptive resin;

(e) washing the adsorbed lignan containing extract with an aqueous diluent;

(f) eluting the lignan containing extract; thereby obtaining a lignan containing compound; and optionally, (g) adjusting the pH of the released lignan before drying.

Further aspects of the invention are directed to compositions and formulations containing the lignan component obtained from the above described processes and methods of using the compositions and formulations.

The objectives and advantages of the present invention will be clear from the description that follows.

DETAILED DESCRIPTION OF THE INVENTION

Figure 1:
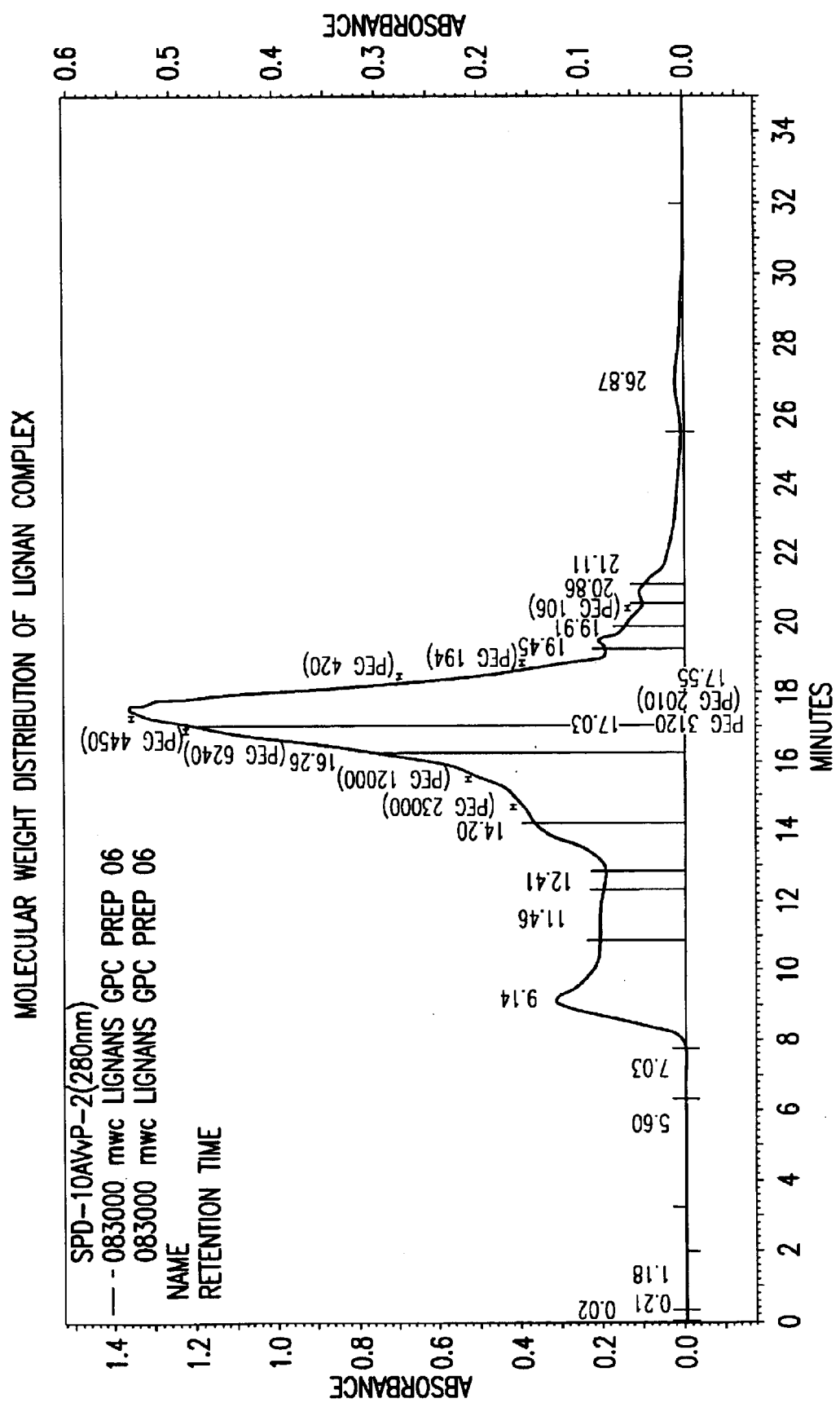
FIG. 1 shows a chromatograph from the column chromatography assay which shows the molecular weight distribution of the lignan complex. The bulk of the complex is constituted with components less than 12,000 Dalton in molecular weight. Representative molecular weight markers of polyethylene glycol are shown on the chromatogram to estimate the molecular weights of different fraction of the product. Hereafter Lignan Complex refers to a plant extract containing a lignan from plant material, the principal among which is SDG.
Figure 4:
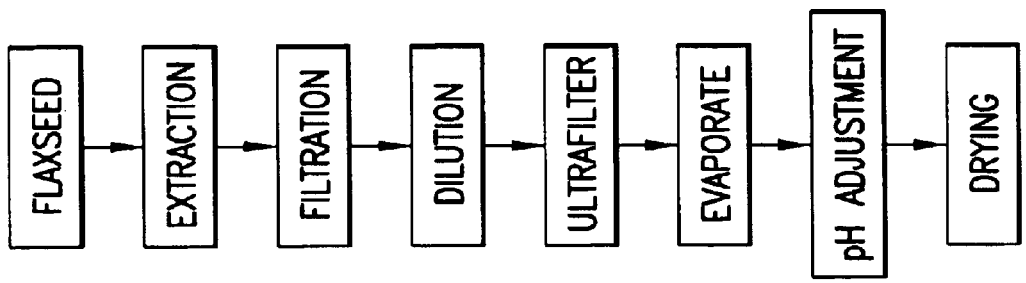
FIGS. 2–7 show various variations of the extraction process of the present invention.
Figure 3:
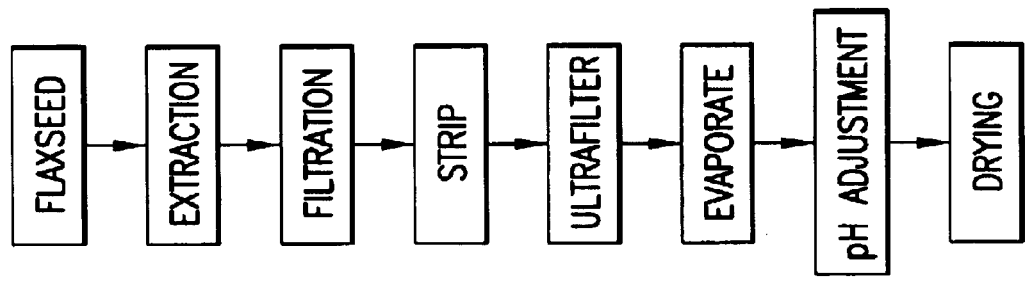
Figure 2:
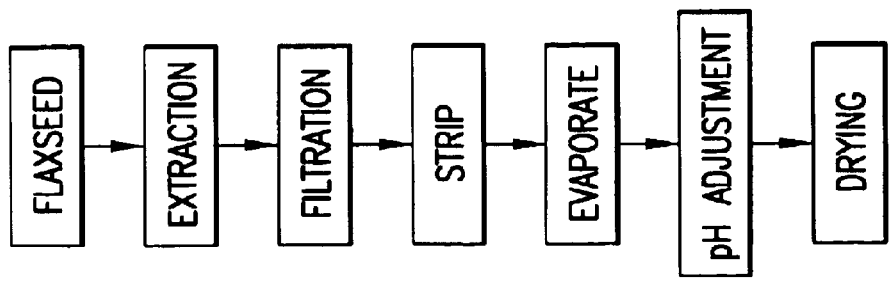
Figure 7:
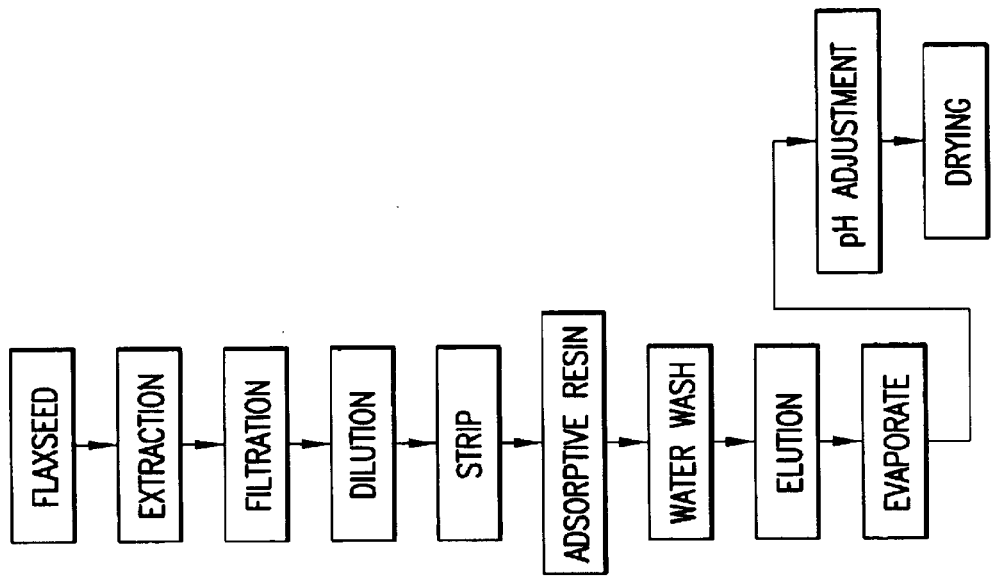
Figure 6:
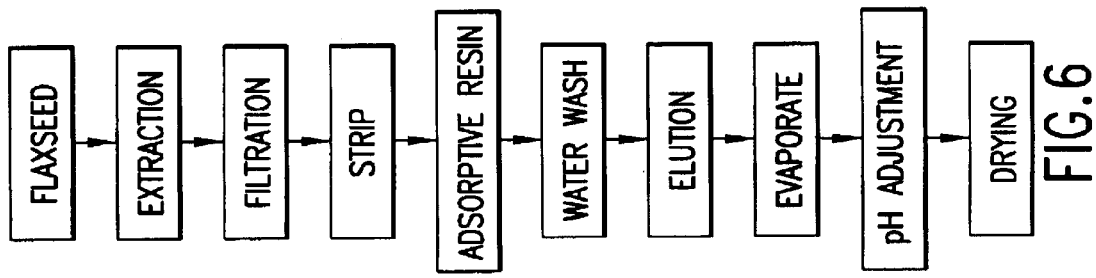
Figure 5:
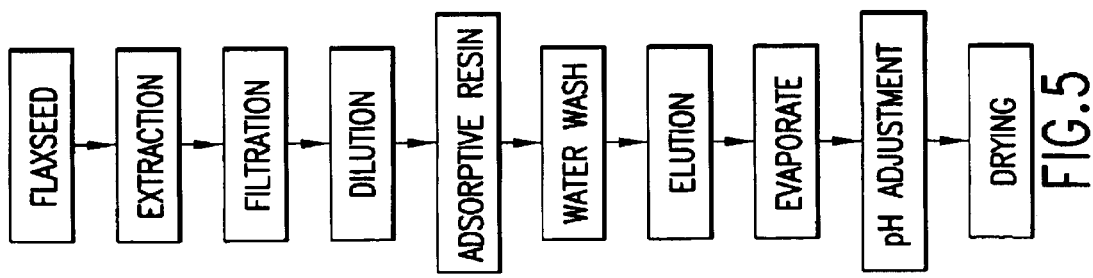

The present invention relates to a process for obtaining lignan from plant materials. In one embodiment, the present invention relates to a process for obtaining lignan comprising:

(a) contacting a lignan containing plant material with an extraction solvent to obtain an extraction solution comprising a lignan containing extract and the extraction solvent;

(b) separating plant material solids from said extraction solution;

(c) reducing microbial component content in said extraction solution obtained in (b);

(d) removing from 0 to 100% of the extraction solvent from the extraction solution, while simultaneously adding an aqueous diluent to the extraction solution;

wherein a lignan is obtained therefrom.

In a preferred embodiment, plant material such as flax, flaxseed or preferably defatted flax, is pulverized by any suitable means such, as grinding, crushing and/or chopping. The pulverized plant material is then extracted with a suitable extraction solvent, such as an alcohol. Preferably the alcohol is an aqueous alcohol and more preferably, an aqueous aliphatic alcohol. A suitable alcohol may be selected from methanol, ethanol or isopropanol, wherein ethanol is particularly preferred. The concentration of the alcohol should be in the range of 50–80% (v/v) as described by Westcott and Muir, "Medicinal Lignans from Flax Seed", Phytochemicals and Phytopharmaceuticals, AOCS Press, Champaign, Ill., 2000, and more preferably 60–70% (v/v).

The extraction is carried out at a suitable temperature, to minimize growth of potentially harmful microbial compounds and facilitate extraction of the lignan complex from the plant material. Suitable temperatures range from between room temperature and the boiling point of the solvent, preferably between 40° C. and 70° C. and, more preferably, between 50° C. and 60° C.

The ratio of extraction solvent to the pulverized plant material should be suitable to permit agitation of the mixture. This ratio is preferably from 4:1 to 8:1 ml solvent per gram of pulverized plant material. A more preferred ratio is from 5:1 to 7:1 ml solvent per gram of pulverized plant material.

The duration of the extraction process is from about 4–8 hours. It is more preferable that the extraction be carried out from between 5 and 7 hours. Where elevated temperatures are used, a 6 hour extraction time is most preferred.

The extraction results in the formation of a slurry comprising the extraction solvent, which contains the desired lignan component, and the solid plant material. After extraction is completed, the liquid fraction of the resulting slurry (hereinafter, extraction solution), which contains the desired lignan complex, is separated from the solid plant material. The separation may be carried out in any suitable manner known of removing solids from a liquid. Examples of suitable techniques include filtration and centrifugation. Where filtration is used, the pore or mesh size of the membrane filters or screens, is selected based on the size of the material being removed. The type of membrane filter selected is based on the compatibility of the membrane filter with the solvent passing through it.

Where the plant material is flax, it has been observed that the flax swells during extraction and consequently absorbs a large amount of solvent at the end of extraction. The slurry, therefore, forms a wet meal cake that is subsequently strained and/or pressed, in order to remove the aqueous alcoholic extract from within the solid plant material component. Thus, in one embodiment of the invention, the wet meal cake is pressed, preferably with a screw press, to obtain the extraction solution. This substantially increases the yield of the lignan complex obtained from the flax wet meal cake.

In order to further increase the yield of the extraction solution, the screw press may also be used following separation of the plant material solids from the extraction solution whereby, for example, filtration or centrifugation is used as a separating technique.

The resulting extraction solution is then further clarified by passing it through a membrane filter to reduce the level of microbial components present in the solution and remove any residual solids not removed from the initial separation.

The preferred type of membrane filter for this clarification step is preferably a nylon filter, however, any suitable type of filter may be used. It is desirable to reduce the amount of microbial material as much as possible. For the present invention, the preferred percent reduction of microbial content is from about 90–100%, preferably 90%; also, preferably 95%, wherein about 98–100% is particularly preferred; and 99.9% is also preferred.

The nylon membrane filter has a pore size of from 0.1–10 μm, and preferably, 0.2–10 μm. A membrane cartridge filter, having a similar pore size rating, may also be use within the meaning of the invention. The resulting clarified extraction solution is further processed according to, but not limited to, one of the embodiments described below.

The alcoholic extraction solvent is subsequently removed (i.e., stripped) from the clarified extraction solution, preferably by evaporation. Applicants have observed that concentration of the extraction solution by evaporation results in the formation of a thick viscous layer which precipitates quickly. It is, therefore, important not to concentrate the extraction solution beyond 10% solids (w/v) since doing so would lead to the formation of a precipitate.

In order to avoid this undesirable effect of evaporating the extraction solvent, and to allow favorable subsequent processing of the desired extract, an aqueous diluent is added to dilute the extraction solution during the evaporation/stripping of the extraction solvent. The preferred aqueous diluent is water. Therefore, all of the extraction solvent present in the extraction solution can be removed if desired. In this way, the desired dilution of the extract is maintained by the addition of water during the evaporation/stripping procedure.

The resulting aqueous extraction solution (i.e., the aqueous supernatant layer) is then dried to obtain a light green hygroscopic powder. Drying may be carried out by any suitable method, such as evaporation or spray drying. Size exclusion chromatography shows that the resulting lignan complex has a large molecular weight distribution, with the bulk of the constituents having a molecular weight below 12,000 Dalton.

In order to obtain a less hygroscopic product, in another embodiment of the invention, after reduction of the alcohol content in the clarified extraction solution, by for example dilution and/or evaporation, the resulting extraction solution is subjected to ultrafiltration in order to remove sugars (e.g. cyanogenic glycosides) present therein. Ultrafiltration is carried out using at least two filter volumes of an aqueous diluent to remove cyanogenic sugars and other undesirable compounds. The preferred aqueous diluent is water.

Suitable ultrafiltration membrane filters include organic polymers or copolymers, such as polysulfone, polyacrylonitrile, cellulose acetate, or inorganic materials such as zirconia, alumina or ceramic materials. Based on the molecular weight distribution of the desired lignan product, it is important to use a membrane filter with a molecular weight cutoff (MWCO) of less than 5,000, more preferably a 1,000 MWCO membrane filter.

Due to poor stability of polymeric membranes in high concentration alcohol solutions (Shukla, R. Ph.D. Thesis, University of Illinois at Urbana-Champaign, 2000) it is also desirable to lower the alcohol concentration either by dilution with water or by stripping the alcohol, preferably by evaporation. Thus, the resulting reduced alcohol content extraction solution does not have a negative effect on the performance of the membrane filter.

The resulting ultrafiltered retentate is substantially free of cyanogenic sugars and contains the desired lignan in a relatively purified form. The ultrafiltered retentate is then dried, either directly or after further concentration by evaporation or spray drying, for example.

It has been found that adjusting the pH of the product containing the lignan prior to the drying step facilitates the drying process. In a preferred embodiment, the process of obtaining a lignan further comprises adjusting the pH of the lignan containing product prior to drying said product. The pH can be adjusted by using any suitable acid or alkali reagent. In a more preferred embodiment, the pH is adjusted to between about 3.0 to about 9.0 before drying.

Most preferably, the pH is from between about 7.5 to about 8.0.

In another aspect of this particular embodiment, the extraction solution obtained from step (c) is diluted with an aqueous diluent and, instead of removing the extraction solvent in accord with step (d), the diluted extraction solution is subjected to ultrafiltration to remove sugars and other impurities.

In another embodiment, the invention provides a process for obtaining lignan comprising:

(a) contacting a lignan containing plant material with an extraction solvent to obtain an extraction solution comprising a lignan containing extract and the extraction solvent;

(b) separating plant source solids from said extraction solution;

(c) reducing microbial component content in said extraction solution obtained in (b);

(d) contacting the extraction solution obtained in (c) with an adsorptive resin;

(e) washing the adsorbed lignan containing extract with an aqueous diluent;

(f) eluting the lignan containing extract; thereby obtaining a lignan therefrom; and optionally, (g) adjusting the pH of the released lignan before drying.

In this embodiment, steps (a) through (c) are carried out as described above. The clarified extraction solution obtained from step (c) is treated with an adsorptive resin, in either a batch or continuous column chromatography type process. The extract obtained from the step (c) is applied to the adsorptive resin and then washed with an aqueous diluent to remove cyanogenic sugars and other impurities. The preferred aqueous diluent is water.

Next, the adsorbed lignan complex is eluted with aqueous alcohol (20–100% by volume at 25–85° C.) in either a gradient or a single percentage process. The alcohol may be selected from, but is not limited to, methanol, ethanol or isopropanol. Ethanol is a preferred alcohol for releasing the adsorbed lignan containing extract from the resin. The resulting material is dried by, for example, evaporation or spray drying, in order to produce a product which is approximately 20–45% lignan on a solids basis. It has been found that adjusting the pH of the product of the chromatographic separation does not break down the lignan complex but rather greatly facilitates the drying of said product. The pH can be adjusted with any suitable acid or alkali reagent. In a more preferred embodiment, step (g) is incorporated into the process. More preferably, step (g) comprises adjusting the pH of the released lignan complex to between about 3.0 to about 9.0 before drying the product. Most preferably, the pH is from between about 7.5 to about 8.0.

Suitable resins may be selected from, but are not limited to, polymethacrylate, ethylvinylbenze-divinylbenzene, styrene-divinylbenzene, polystyrene or phenol formaldehyde polymers, and may be either ionic or non-ionic.

In another aspect of this embodiment, after step (c) and before step (d), the extraction solution obtained from step (c) is diluted with an aqueous diluent, prior to treatment with the adsorptive resin in step (d). The preferred aqueous diluent is water.

In another embodiment, it is desirable to adjust the pH of the extraction solution obtained from step (c) to a value of between about 3.0 to about 9.0. More preferably, the pH is between about 7.5 to about 8.0. It has been found that adjusting the pH accordingly with any suitable acid or alkali reagent does not break down the lignan complex, but rather facilitates the subsequent drying of the lignan product.

Alternatively, in another aspect of this embodiment, after step (c) and before step (d), the extraction solvent present in the extraction solution obtained in step (c) is removed while simultaneously adding an aqueous diluent to said extraction solution. The preferred aqueous diluent for this aspect of the invention is water.

In yet another aspect of this embodiment, after step (c) and before step (d), the process further comprises:
  (i) diluting the extraction solution obtained in step (c) with an aqueous diluent; and
  (ii) removing the extraction solvent from the extraction solution obtained in (i) while simultaneously adding an aqueous diluent to said extraction solution.

The following non-limiting Examples are provided to further described the invention. Those of ordinary skill in the art will appreciate that several variations these Examples are possible within the spirit of the invention.

EXAMPLE 1

Extraction of Lignan Complex

A substantially oil-free flaxseed meal was obtained from Northern Sun, Redwing, Minn. The meal is commercially crushed, solvent extracted to remove oils and dried to remove all residual solvent. The composition of different batches of meal was determined and is shown below.

| Moisture | Protein | Oil | Lignan | Cyanides |
|---|---|---|---|---|
| 9%–10% | 30%–36% | 0.3%–1% | 1%–3.5% | 300 mg/kg–600 mg/kg |

17 kg of the meal was extracted at 55° C. with 113.5 liters of 70% (v/v) food grade ethanol. The extraction was carried out by agitation of a meal containing slurry in a stirred tank for a period of not more than 4–6 hours. Subsequent to extraction, the slurry was passed through a screw press fitted with a 50 mesh filter membrane to remove most of the solvent contained in the resulting wet cake. Approximately 76 liters of extract was collected and passed through a 1 μm nylon filter, obtained from Midwest Filter Co., Lake Forest, Ill. The extract was further processed through a 0.2 μm filter (Dominick Hunter, Charlotte, N.C.) to lower the microbial load in the solvent. The resulting filtered extract had the following composition:

| Ethanol (%, v/v) | Lignan (g/l) | Total Solids (g/l) | Purity (%) | Yield (%) |
|---|---|---|---|---|
| 71 | 1.943 | 16.45 | 11.82 | 76.59 |

The resulting filtered extract was processed according to one of the examples shown below. It should be understood that these examples are not intended to limit the scope of the invention.

EXAMPLE 2

Stripping/Drying

A portion of the filtered extract generated in Example I was stripped under vacuum with steam to remove all ethanol present and simultaneously diluted with water to obtain a solution of 10% (w/v) solids. The extract was kept at 60° C. to solubilize the components and prevent microbial growth. The extract was then spray dried. The resulting product was a light green powder, having the following properties:

| Moisture | Protein | Fat | Fiber | Ash | Carbohydrates (free) | Lignan | Standard Plate Count |
|---|---|---|---|---|---|---|---|
| 5.87% | 7.95% | 8.01% | 0.26% | 3.96% | 45.92% | 10.42% | 4200/g |

In order to test the resulting product for the presence of cyanogenic glycosides (sugars), either of a EM Quant assay or a Spectro Quant assay (EM Sciences, Gibbstown, N.J.) was used. These assays detect the presence of free cyanides liberated by the action of a p-glucuronidase enzyme (Sigma Chemical Co., St. Louis, Mo.) on sugars. Consequently, it was determined that the resulting product was free of the presence of any cyanogenic glycosides.

EXAMPLE 3

Ultrafiltration 500 ml of the filtered extract from Example 1 was diluted to 2000 ml with water. The solution was filtered under pressure at 100 psi with a regenerated cellulose based polymeric membrane until the volume of retentate was reduced to 1100 ml. The composition of the different fractions appears in the table below.

| Sample | Volume | Ethanol (%) | Lignan (g/l) | Total Solids (g/l) | Purity (%) | Yield (%) |
|---|---|---|---|---|---|---|
| Feed | 2000 ml | 13 | 0.6 | 3.68 | 1.63 | — |
| Permeate | 900 ml | 13 | 0.22 | 2.48 | 8.11 | 16.57 |
| Retentate | 1100 ml | 16 | 0.9 | 3.88 | 23.32 | 82.95 |

The retentate fraction was dried to a light yellow free flowing powder, and determined to be free of cyanogenic glycosides.

EXAMPLE 4

Ultrafiltration

A portion of the feed from Example 1 was stripped of ethanol without dilution under vacuum with steam to generate an extract with the following composition:

| Ethanol (%, v/v) | Lignan (g/l) | Total Solids (g/l) | Purity (%) |
|---|---|---|---|
| 0.63 | 1.31 | 16.28 | 8.08 |

This extract was further diluted with water to generate the following diluted feed:

| | | | |
|---|---|---|---|
| 0.15 | 0.381 | 3.55 | 10.73 |

310 ml of this feed was ultrafiltered under pressure of 100 psi to with a polymeric membrane rated for 15% sodium chloride rejection to generate 200 ml of permeate.

The composition of the different streams was determined as follows:

| | Volume | Ethanol (%, v/v) | SDG (g/l) | Total Solids (g/l) | Purity (%) | Yield (%) |
|---|---|---|---|---|---|---|
| Feed | 310 ml | 0.15% | 0.381 | 3.55 | 10.73 | — |
| Permeate | 200 ml | 0.15% | 0.015 | 0.17 | 8.82 | 2.54 |
| Retentate | 110 ml | 0.16% | 0.6091 | 4.15 | 14.67 | 56.7 |

The retentate fraction was dried to a free flowing powder, and determined to be free of cyanogenic glycosides.

EXAMPLE 5

Adsorption and Recovery of Lignans from Resin

A glass liquid-chromatography column (2.54 cm I.D.) was slurry packed in DI water with ADS 400 (Thermax Limited, Novi, Mich.) nonfunctional methacrylic polymer resin. The resin was cleaned with 400 ml of 70% (v/v) ethanol followed by 400 ml water. The resin was then back flushed with water until the resin bed volume expanded by about one-half of its original packed volume in order to partition the resin by size. The final packed volume was 100 ml.

500 ml of the filtered extract from Example 1 was diluted to 2000 ml with water. At a temperature of 60° C., 20 column volumes (or 2000 ml) were fed through the resin bed at 6 column volumes/hour or 10 ml/minute. The resin bed was subsequently washed with 200 ml of water at 10 ml/minute to remove residual sugars and other impurities. The remaining lignan complex was then eluted from the resin with 70% ethanol at 10 ml/minute (total volume=400 ml).

The composition of the resulting streams appears below.

| | Ethanol (%) | Lignan (g/l) | Total Solids (g/l) | Purity (%) | Yield (%) |
|---|---|---|---|---|---|
| Feed | 16 | 0.55 | 3.98 | 13.96 | — |
| Product | 55.17 | 2.3 | 6.36 | 36.16 | 82.84 |

The product fraction was dried to a light green free flowing powder, and determined to be free of cyanogenic glycosides.

EXAMPLE 6

Adsorption and Recovery of Lignans from Resin

The packed column in Example 5 was washed with 200 ml of 70% ethanol and 200 ml water. 25 column volumes (2500 ml) of the diluted feed from Example 4 were fed to the column at a constant flow rate of 12 ml/min at 60° C. The resin was washed with 220 ml water at 12 ml/minute to remove residual sugars and other impurities. The resulting lignan complex was then eluted from the resin with 70% ethanol at 12 ml/minute (total volume=400 ml). The composition of the resulting streams appears below.

| | Ethanol (%) | Lignan (g/l) | Total Solids (g/l) | Purity (%) | Yield (%) |
|---|---|---|---|---|---|
| Feed | 0.15 | 0.38 | 3.55 | 10.73 | — |
| Product | 56 | 2.01 | 5.24 | 38.41 | 84.61 |

The product fraction was dried to a light green free flowing powder, and determined to be free of cyanogenic glycosides.

EXAMPLE 7

A glass liquid-chromatography column was slurry packed in DI water with Rohm and Haas XAD 761 (Rohm and Haas Inc., Philadelphia Pa.) non functional phenol formaldehyde resin using the procedure described in Example 5.

500 ml of the filtered extract from Example 1 was diluted to 3000 ml with DI water. At a temperature of 60° C., 30 column volumes (or 3000 ml) were fed through the resin bed at 6 column volumes/hour or 10 ml/minute. The resin bed was subsequently washed with 200 ml of water at 10 ml/minute to remove residual sugars and other impurities. The remaining lignan complex was then eluted from the resin with 70% ethanol at 10 ml/min (total volume=500 ml).

The composition of the resulting streams appears below.

| | Ethanol (%) | Lignan (g/l) | Total Solids (g/l) | Purity (%) | Yield (%) |
|---|---|---|---|---|---|
| Feed | 12 | 0.447 | 3.57 | 12.54 | — |
| Product | 55.17 | 1.437 | 3.04 | 41.46 | 53.49 |

The product fraction treated with 0.1% (w/v) Sodium Hydroxide to raise the pH to 7.6 and spray dried to a light green free flowing powder. It was determined to be free of cyanogenic glycosides.

EXAMPLE 8

A glass liquid-chromatography column was slurry packed in DI water with Rohm and Haas XAD 1180 (Rohm and Haas Inc., Philadelphia Pa.) non functional resin using the procedure described in Example 5.

500 ml of the filtered extract from Example I was diluted to 2000 ml with DI water. At a temperature of 60° C., 20 column volumes (or 2000 ml) were fed through the resin bed at 6 column volumes/hour or 10 ml/minute. The resin bed was subsequently washed with 200 ml of water at 10 ml/minute to remove residual sugars and other impurities. The remaining lignan complex was then eluted from the resin with 70% ethanol at 10 ml/min (total volume=500 ml).

The composition of the resulting streams appears below.

|  | Ethanol (%) | Lignan (g/l) | Total Solids (g/l) | Purity (%) | Yield (%) |
|---|---|---|---|---|---|
| Feed | 12 | 0.589 | 4.48 | 13.17 | — |
| Product | 55.17 | 1.292 | 3.44 | 37.58 | 54.79 |

The product fraction was dried to a light green free flowing powder, and determined to be free of cyanogenic glycosides.

EXAMPLE 9

A glass liquid-chromatography column was slurry packed in DI water with Thermax ADS800 (Thermax Inc., Novi Mich.) non functional styrene divinyl benzene resin using the procedure described in Example 5.

500 ml of the filtered extract from Example I was diluted to 3000 ml with DI water. At a temperature of 60° C., 30 column volumes (or 3000 ml) were fed through the resin bed at 6 column volumes/hour or 10 ml/minute. The resin bed was subsequently washed with 200 ml of water at 10 ml/minute to remove residual sugars and other impurities. The remaining lignan complex was then eluted from the resin with 70% ethanol at 10 ml/min (total volume=500 ml).

The composition of the resulting streams appears below.

|  | Ethanol (%) | Lignan (g/l) | Total Solids (g/l) | Purity (%) | Yield (%) |
|---|---|---|---|---|---|
| Feed | 12 | 0.537 | 3.97 | 13.53 | — |
| Product | 55.17 | 2.937 | 3.04 | 38.03 | 46.54 |

The product fraction was dried to a light green free flowing powder, and determined to be free of cyanogenic glycosides.

EXAMPLE 10

Acid Preparation and Recovery of Lignans

A portion of the extract prepared in Example 2 was diluted 1:1 by volume with deionized water and treated with 1% Sulfuric Acid to adjust te pH to 3.5 at room temperature. At this temperature the extract exhibited flocculation and separated into two distinct phases. The top clear phase was removed by centrifugation and the bottom precipitate was collected and dried.

Analysis of the two phases is shown below.

|  | SDG (g/l) | Dry Solids (g/l) | Purity (%) |
|---|---|---|---|
| Feed | 2.04 | 20.5 | 9.95 |
| Centrifuge Overs | 1.264 | 17.75 | 7.12 |
| Centrifuge Unders | 6.4 | 30.41 | 21.04 |

Hence purity of lignans was increased by selective precipitation.

Once obtained from the above described methods, the lignan product may be incorporated into food or pharmaceutical formulations. The formulations may be prepared for any route of administration to humans or animals, however, oral delivery formulations are preferred. Typical formulations comprising the obtained lignan may comprise from: 15–25 wt. % of the lignan product obtained from any of the above described methods; 60–84 wt. % of a filler component; and 1–25 wt. % of a dietary supplemental nutrient.

All publications mentioned hereinabove are hereby incorporated in their entirety by reference.

While the forgoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A process for obtaining lignan comprising:
   (a) contacting a lignan containing plant material with an extraction solvent to obtain an extraction solution comprising a lignan containing extract and said extraction solvent;
   (b) separating plant material solids from said extraction solution;
   (c) reducing microbial component content in said extraction solution obtained in (b);
   (d) removing the extraction solvent from said extraction solution obtained in (c), while simultaneously adding an aqueous diluent to said extraction solution;
   wherein lignan is obtained therefrom.

2. The process according to claim 1, wherein said extraction solvent is an alcohol.

3. The process according to claim 2, wherein said alcohol is selected from the group consisting of methanol, ethanol and isopropanol.

4. The process of claim 3, wherein said alcohol is ethanol.

5. The process according to claim 1, wherein said separating step (b) comprises filtration or centrifugation.

6. The process according to claim 5, wherein after said separating step (b), plant material solids are further subjected to a screw press to obtain additional extraction solution therefrom.

7. The method of claim 5, wherein said separating step (b) comprises filtration.

8. The process according to claim 1, wherein said extraction solvent is removed by evaporation.

9. The process according to claim 1, wherein said aqueous diluent is water.

10. The process according to claim 1, further comprising removing sugars from the extraction solution obtained in (d).

11. The process according to claim 10, wherein said sugars are removed from the extraction solution obtained in (d) by ultrafiltration.

12. The process according to claim 11, wherein said ultrafiltration is conducted with a membrane filter having a pore size of 1,000–5,000 MWCO.

13. The process according to claim 11, wherein said obtained lignan is dried by evaporation or spray drying.

14. The process according to claim 1, wherein the lignan containing plant material is flax.

15. The process according to claim 1, wherein the removal of the extraction solvent and simultaneous addition of an aqueous diluent to the extraction solution results in a concentration of extraction solvent of less than 20% by weight of the original extraction solvent.

16. The process of claim 13, further comprising adjusting the pH of the lignan to between about 3.0 to about 9.0 prior to drying said lignan.

17. The process of claim 16, wherein said pH is between about 7.5 to about 8.0.

* * * * *

UNITED STATES PATENT AND TRADEMARK OFFICE
CERTIFICATE OF CORRECTION

PATENT NO. : 6,767,565 B2
DATED : July 27, 2004
INVENTOR(S) : Shukla et al.

It is certified that error appears in the above-identified patent and that said Letters Patent is hereby corrected as shown below:

Column 5,
Line 11, delete "use," and substitute therefor -- used --.

Column 7,
Line 35, delete "described" and substitute therefor -- describe --.
Line 36, delete "variations these" and substitute therefor -- variations of these --.

Column 8,
Line 15, delete "Example I" and substitute therefor -- Example 1 --.

Column 9,
Line 8, insert the headings -- Ethanol (%, v/v) Lingan (g/l) Total Solids (g/1) Purity (%) --.
Line 11, delete "to".

Column 10,
Line 59, delete "Example I" and substitute therefor -- Example 1 --.

Column 11,
Line 19, delete "Example I" and substitute therefore -- Example 1 --.
Line 45, delete "te" and substitute therefore -- the --.

Signed and Sealed this

Thirtieth Day of August, 2005

JON W. DUDAS
*Director of the United States Patent and Trademark Office*

UNITED STATES PATENT AND TRADEMARK OFFICE
CERTIFICATE OF CORRECTION

PATENT NO.    : 6,767,565 B2
DATED         : July 27, 2004
INVENTOR(S)   : Shukla et al.

It is certified that error appears in the above-identified patent and that said Letters Patent is hereby corrected as shown below:

<u>Title page,</u>
Item [75], Inventors, delete "Ahmad K. Hilaly".

Signed and Sealed this

Twenty-eighth Day of March, 2006

JON W. DUDAS
*Director of the United States Patent and Trademark Office*